US005733904A

United States Patent [19]

Fujii et al.

[11] Patent Number: 5,733,904
[45] Date of Patent: Mar. 31, 1998

[54] METHOD FOR PREVENTION AND TREATMENT OF VIRAL INFECTIOUS DISEASES FOR VIRAL SUPPRESSION

[75] Inventors: Yoichi Fujii, Nagoya; Akio Adachi, Tokushima; Toshio Asano, Mishima, all of Japan

[73] Assignee: Asahi Kasei Kogyo Kabushiki Kaisha, Osaka, Japan

[21] Appl. No.: 815,669

[22] Filed: Mar. 10, 1997

[30] Foreign Application Priority Data

Apr. 10, 1996 [JP] Japan ................. 8-088233

[51] Int. Cl.[6] ................................ A61K 31/55
[52] U.S. Cl. ................................ 514/218
[58] Field of Search ........................ 514/218

[56] References Cited

U.S. PATENT DOCUMENTS 4,678,783  7/1987  Hidaka et al. .................. 514/218

FOREIGN PATENT DOCUMENTS

WO 93/19766  10/1993  WIPO .

OTHER PUBLICATIONS

M. Nokta et al., "X–Irradiation Enhances In Vitro Human Immunodeficiency Virus Replication Correlation with Cellular Levels of cAMP", *X–Ray Enhances HIV Replication*, pp. 402–408, 1992.

S. Patzold et al., "Novel indolocarbazole protein kinase C inhibitors prevent reactivation of HIV–1 in latently infected cells", *Antiviral Research*, 22, 1993, pp. 273–283.

N. Mohagheghpour et al., "Early Activation Events Render T Cells Susceptible to HIV–1–induced Syncytia Formation", *The Journal of Biological Chemistry*, vol. 266, No. 11, Apr. 1991, pp. 7233–7238.

M. Kurokawa et al., "Inhibitory effect of protein kinase C inhibitor on the replication of influenza type A virus", *Journal of General Vitology*, 1990, pp. 2149–2155.

*Primary Examiner*—Jerome D. Goldberg
*Attorney, Agent, or Firm*—Young & Thompson

[57] ABSTRACT

A method for prevention and treatment of viral infectious diseases using a medicament containing an effective amount of a compound of the formula

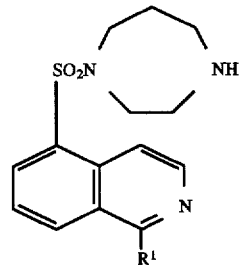

where $R^1$ is hydrogen or hydroxy, or acid addition salt thereof.

31 Claims, 5 Drawing Sheets

F I G. I

5,733,904

METHOD FOR PREVENTION AND TREATMENT OF VIRAL INFECTIOUS DISEASES FOR VIRAL SUPPRESSION

This application corresponds to Japanese application 8-088233 of Apr. 10, 1996, the disclosure of which is incorporated herein by reference.

FIELD OF THE INVENTION

This invention relates to a method for prevention and treatment of viral infectious diseases and for viral suppression.

PRIOR ART

A virus is a particle-size microbe consisting of any one of a number of nucleic acids of DNA or RNA and a small number of protein molecules. Viruses per se are known to have no propagation activities and are able to grow by using the metabolic systems of host cells after infiltrating the cells of animals, bacteria, fungi, algae or plants. Viral genes contain proteins necessary for infection, proteins (enzymes) necessary for the expression of nucleic acids in the host cells and proteins essential for holding viral structure.

The symptoms appearing in viral infections depend on the types of viral species. The same virus sometimes leads to different symptoms on the one hand and the different types of virus can cause similar symptoms on the other hand. Viral infection does not always show symptoms, and there are many cases without symptoms (latent infection). If the symptoms appear, possible manifestations range from the appearance of all the disease conditions to the appearance of only a part of the disease conditions. The reasons why these diversities occur have not been clarified; however, it may be that it depends on the type of virus and the conditions of the immunological functions of the infected hosts.

Viruses in animals are classified into DNA viruses and RNA viruses depending upon the constituent gene in the viral particles, and are given the generic name animal virus.

The replication of genes and the mechanism of transcription in DNA virus and RNA virus are different, but the processes for infection of animal virus and growth in the cells are substantially similar to each other.

Namely, the following processes are common:

(1) attachment, penetration and uncoating of the virus to the surface of the cells, (2) duplication and transcription of nucleic acid, (3) synthesis and processing of viral protein, and (4) maturation and release of viral particles.

By these processes, viral proliferation in animals for the establishment of viral infectious diseases proceeds, and results in damage and death of the host cells.

Heretofore, amantadine and rimantadine have been used for prevention and treatment of viral infectious diseases. These medicaments inhibit the membrane fusion that is necessary for penetration of viral particles by increasing the pH level of intracellular ribosomes to inhibit cleavage of viral envelope membranes by protease. Aciclovir, ganciclovir, penciclovir and foscarnet sodium are known to inhibit viral DNA duplication. Ribavirin and bredinin inhibit transcription and duplication (RNA→RNA) of RNA viruses. Neplanocin A and aristeromycin inhibit methylation of the mRNA cap of a virus to decrease the translation rate of the mRNA and thereby suppress viral proliferation.

Human immunodeficiency virus (HIV) and hepatitis C virus (HCV) produce structurally functional proteins by cleavage of synthetic peptide by originating protease from their own genom. Substances which specifically inhibit the protease activity have been studied. Indinavir and crixivan are protease inhibitors which inhibit cleavage of pre-protein of HIV by protease to thereby suppress activation of the pre-protein and thereby suppress viral proliferation. 2–5 oligoadenylate accumulated in the cells by action of interferon stimulates decomposition of viral mRNA by increasing RNase activity to inhibit translation to viral protein.

Inhibitors of reverse transcriptase activity (RNA→DNA), such as 3'-azido-3'-deoxythymidine (hereinafter "AZT"), 2', 3'-dideoxycytidine (hereinafter "ddC") and 2', 3'-dideoxyinosine (hereinafter "ddI") are used for the treatment of AIDS.

Reverse transcriptase is an enzyme which catalyses DNA synthesis by template of RNA, and is found endogenously in a virus. Allosteric reverse transcriptase inhibitors, such as 5-ethyl-6-phenylthiouracyl and nevirapine, bind to different parts of a substrate's binding site for reverse transcriptase to inhibit reverse transcriptase activity.

Although C kinase inhibitor H-7 [1-(5-isoquinorylsulfonyl)-2-methyl-piperazine] has not been found to be clearly effective against HIV infectious disease, its relationship is known (Antiviral Res., 22: 273–283, 1993).

Although many trials have been conducted, no complete cure for viral infectious diseases have been established, except in the case of smallpox whose extermination was announced by WHO due to the development of an effective vaccine. New medicaments effective for prevention and treatment of viral infectious disease are desired.

DESCRIPTION OF THE PREFERRED EMBODIMENTS

Figure 1:
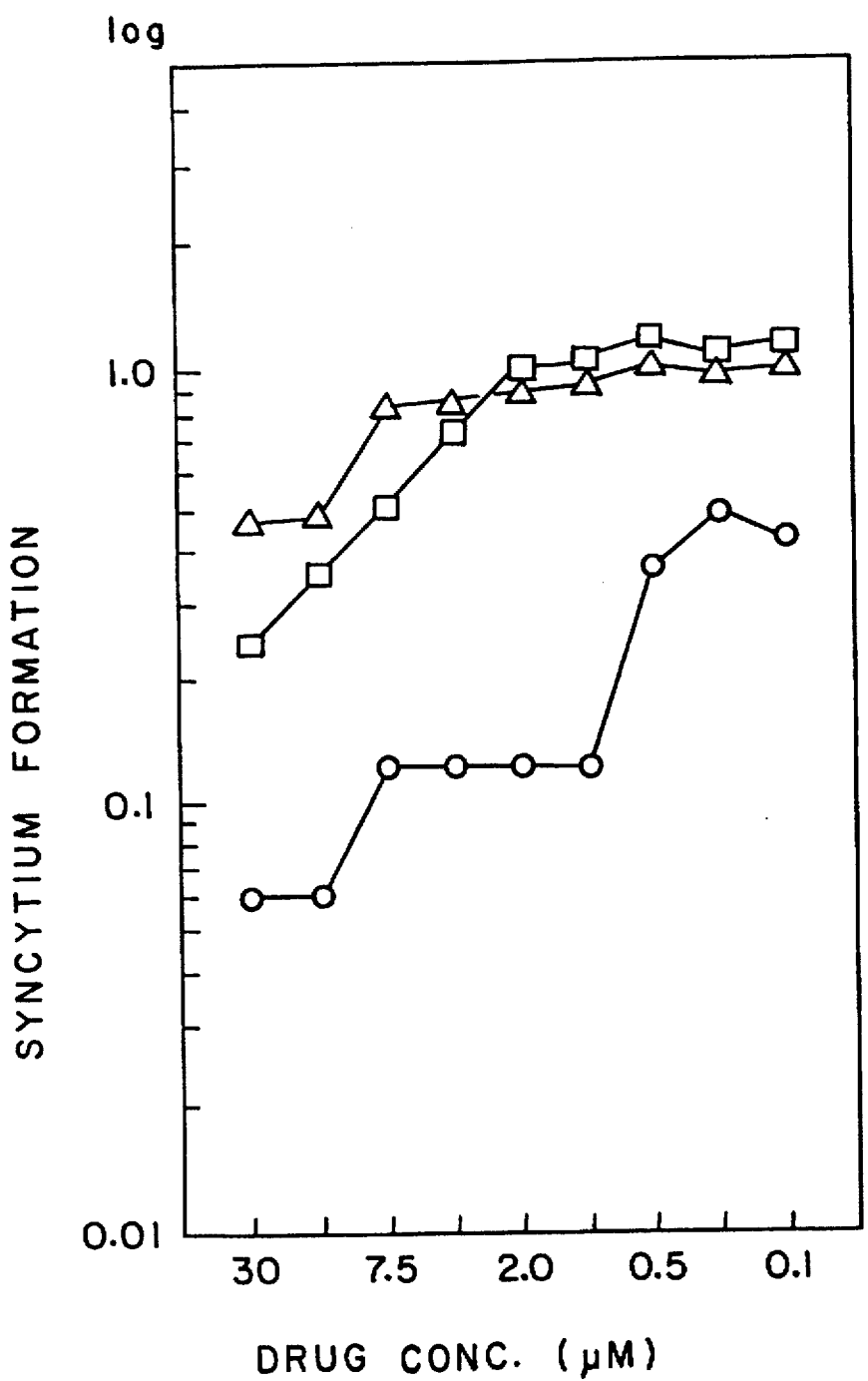
FIG. 1: action of the compound (result of assay on the inhibitory activity for syncytium formation) on acute phase infection caused by HIV-1 in Example 3.

We have found as a result of extensive studies that a compound of the formula [I] below, or acid addition salt thereof, showed excellent preventive and curative effects on viral infectious diseases and was useful for improving medicaments. The present invention has been completed by the above findings.

An object of the present invention is to provide a medicament for prevention and treatment of viral infectious diseases comprising a compound of formula [I]

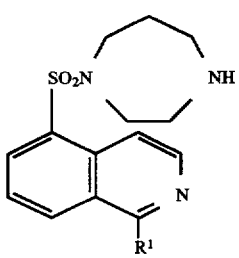

where R¹ is hydrogen or hydroxy, or an acid addition salt thereof as an active ingredient.

It has been known that the compound of formula [I] where R¹ is hydrogen or hydroxy, showed vasodilating activity, etc., and was a useful vasodilator, etc., (Japanese Patent Examined Publication No. 7-80854, Japanese Patent Unexamined Publication No. 61-152658, ibid. No. 61-227581, ibid. No. 2-256617, ibid. No. 4-264030, ibid. No. 6-056668, ibid. No. 6-080569, ibid. No. 6-292643, ibid. No. 7-277979, Brit. J. Pharmacol., 8, 1091 (1989), J. Pharmacol. Exp. Ther., 259, 738 (1991), Eur. J. Pharmacol., 195, 267 (1991) and Biochem. Pharmacol., 46, 1487 (1993)).

The compound of formula [I], or acid addition salt thereof, is known. An acid addition salt of the compound of formula [I], where R¹ is hydrogen, is known as fasudil hydrochloride (FAS; hexahydro-1-(5-isoquinoline-sulfonyl)-1H-1,4-diazepine hydrochloride), has been commercially distributed, and is known to have low toxicity. Further, the fact that FAS showed inhibitory action on protein phosphorylation, such as myosin light chain kinase inhibition and C kinase inhibition, is known (Cranial Nerve, 45 (9), 819–824, 1993).

In spite of the above findings, the effect of the present invention on prevention and treatment of viral infectious diseases has never been known.

The present invention is a method for prevention and treatment of viral infectious diseases which includes the step of administering a medicament containing an effective amount of a compound of formula [I].

The compound of formula [I] used in the present invention can be synthesized by the methods disclosed, for example, in Chem. Pharm. Bull., 40 (3), 770–773 (1992) and Japanese Patent Unexamined Publication No. 61-152658. An acid addition salt thereof is preferably a pharmacologically acceptable salt, for example an inorganic salt such as hydrochloride, hydrobromide, phosphate and sulfate, or an organic salt such as acetate, citrate, taratrate, lactate, succinaate, fumalate, maleate and methanesulfonate.

A medicament for prevention and treatment of viral infectious diseases of the present invention can be prepared by mixing the compounds of formula [I], or acid addition salt thereof, and known pharmacologically acceptable carriers.

Examples of the carriers are: gelatin, lactate, a saccharide such as glucose, corn, a starch such as wheat, rice or corn starch, a fatty acid such as stearic acid, calcium stearate, a fatty acid salt such as magnesium stearate, talc, plant oil, steary alcohol, an alcohol such as benzyl alcohol, gum, and polyalkylene glycol.

Examples of a liquid carrier are: water, physiological saline, a sugar solution such as dextrose and others, and glycols such as ethylene glycol, propylene glycol, polyethylene glycol and polypropylene glycol.

Capsules of the medicament for prevention and treatment of viral infectious diseases of the present invention are preferably prepared using gelatine.

Administration of the medicament of the present invention can be made perorally or parenterally. Formulations preferable for peroral administration are tablets, capsules, powder, granules, solutions or elixirs and those for parenteral administration are solutions.

Parenteral administration, such as by intramuscular injection, intravenous injection or subcutaneous injection, are performed in the form of an aseptic solution of the compound of formula [I], or acid addition salt thereof, to which sodium chloride, glucose and other solutes are added to prepare an isotonic solution.

The compound administered by injection is preferably dissolved with sterilized water, lidocaine hydrochloride solution (for intramuscular injection), physiological saline, glucose solution, a solution for intravenous injection and an electrolyte solution (for intravenous injection). The solution may be prepared with 0.001–20 weight percent of an active ingredient, and preferably 0.01–10 weight percent of an active ingredient. Preparations for peroral administration in the form of tablets, capsules, powder or granules contain, for example 0.01–100 weight percent of an active ingredient, and preferably 1–40 weight percent of an active ingredient. A preferred example for peroral administration in the form of a solution is a suspension or a syrup containing 0.01–20 weight percent of an active ingredient. Examples of carriers are aqueous fillers such as perfume, syrup or pharmaceutical micelle.

The dosage of the medicament of the present invention should be determined based on the patient's age, physical condition, body weight, symptoms, types of other treatments if any, number of such other treatments, characteristics of the desired effect, route of administration and dosage regimen. The dosage is generally 0.01–25 mg/kg/day for peroral administration; preferably above 0.5 mg/kg/day, more preferably above 1–2 mg/kg/day and most preferably above 4 mg/kg/day. The preferred dosage for parenteral administration is above 0.1 mg/kg/day, more preferably above 1 mg/kg/day and most preferably above 2 mg/kg/day.

The medicament of the present invention shows, most surprisingly, antiviral activities in various tests and is effective as a medicament for prevention and treatment of viral infectious diseases.

Viral infectious diseases, for which antiviral chemotherapy is required, are for example as follows (Modern Systematic Internal Medicine, Vol. 26, p. 73–88):

Acute viral infectious diseases caused by infection of respiratory syncytial (RS) virus, parainfluenza virus, influenza virus, rhinovirus, adenovirus and rotavirus. Serious relapsing viral infectious diseases in the immunosuppressive state caused by infection of herpes simplex virus, varicella-zoster virus, cytomegalovirus, EB virus and human herpesvirus 6. Viral infectious diseases which become chronic or carrier, caused by infection of hepatitis B virus, hepatitis C virus, HIV and HTLV. Viral infectious diseases with transovarial transmission such as rubella virus. Hemorrhagic fever viral infectious diseases such as Ebola, Lassa fever and hemorrhagic fever with renal syndrome. Infectious diseases caused by retrovirus such as pathogenic virus (HIV) of AIDS (acquired immuno-deficiency syndrome) and pathogenic virus (HTLV) of human T-cell leukemia (Field of Chemotherapy, 11 (6), 1069–1078, 1985, Protein, Nucleic Acid and Enzyme, 40 (9), 1079–1091, 1991). (Retrovirus is a term denoting an RNA virus having reverse transcriptase.) Pathogens of retroviral infectious diseases, adult T-cell leukemia and AIDS.

A target of the medicament of the present invention is preferably the infectious diseases caused by retrovirus (retroviral infectious diseases), and more preferably HIV infectious disease such as AIDS and adult T-cell leukemia.

The present invention also includes a preparation for suppressing viral infection or a preparation for suppressing viral transmission comprising a compound of formula [I], where $R^1$ is hydrogen or hydroxy, or acid addition salt thereof as an active ingredient.

The present invention further includes a preparation for suppressing viral proliferation comprising a compound of formula [I], where $R^1$ is hydrogen or hydroxy, or acid addition salt thereof as an active ingredient.

The present invention still further includes a preparation for suppressing Env protein expression comprising a compound of formula [I], where $R^1$ is hydrogen or hydroxy, or acid addition salt thereof as an active ingredient.

The present invention further yet includes a preparation for suppressing viral generation comprising a compound of formula [I], where $R^1$ is hydrogen or hydroxy, or acid addition salt thereof as an active ingredient.

A term "suppressing viral generation" means suppression of release of viral particles from infected cells. The preparation of the present invention is effective in this suppressing action.

The present invention also includes a preparation for suppressing formation of viral syncytia comprising a compound of formula [I], where $R^1$ is hydrogen or hydroxy, or acid addition salt thereof as an active ingredient.

The present invention also includes a method which uses the preparation to suppress the above-mentioned viral actions.

The compound used in the present invention suppresses cell death or apoptosis caused by the infection of a virus, and is useful for the treatment of viral infectious diseases such as HIV.

The general method used to test the invention is as follows:

MOLT-4 cells (Kikukawa, R. et al., J. Virol. 57 1159-1162, 1986), which were previously subcultured at 37° C. in 5% $CO_2$, where suspended in a culture liquid [RPMI medium (Nissui Co.) and combined with 10% fetal bovine serum (JRH Bioscience Inc.)] to prepare a cell suspension. The cell suspension containing $2\times10^6$ cells was divided into 25 ml culture flasks. A preferable amount of HIV2/GH123 (Shibata, R. et al., J. Virol. 64: 742-747, 1990) was added to infect the cells. The culture liquid was added thereto so that each flask contained 10 ml. Aqueous solutions containing known aliquot concentrations of the present compounds (FAS, and the compound of formula [I] where $R^1$ is hydroxy), each 20 μl, were added to provide a test group. A control group without the compound was also provided. Culture supernatant, 5 ml, was changed every 3-4 days following infection. The medicament was previously dissolved in the culture liquid in order to keep a constant concentration of the compound in the test group. The test compound was also added to MOLT-4 cells without the viral infection, and these cells were cultured for as long as the infected cells to detect the effect of the present compounds on the cells. After 25-30 days, all of the cells were gently stirred and cell suspensions of 100 μl were collected in a 96 hole plate. The number of living cells were counted by an MTT method (Murakami et al., Nippon Rinsho, suppl. HIV Infectious Disease, AIDS, p. 113-119 and Pauwels, R. et al., J. Virol. Methods, 20: 309-321, 1988) to examine the effects of the compounds.

A 5 mg/ml solution of MTT (3-(4,5-dimethyl-2-thiazolyl)-2,5-diphenyl-2H-tetrazolium bromide, Dojin Chem. Inst.), 10 μl was added to the plate, and incubated at 37° C. for 2 hours under 5% $CO_2$ to generate formazan. An isopropanol solution of 10% Triton X and 0.04N hydrochloric acid were added to solubilize the formazan, and the generated formazan was measured at $OD_{550\ nm}$ by a plate reader. The control group were measured at $OD_{630\ nm}$. MTT is converted to formazan having an absorption wave length at 550 nm.

As will be discussed in the examples below, the compound of the present invention suppressed cell death or apoptosis caused by viral infections.

The following examples illustrate the present invention, but are not construed to limit the invention.

EXAMPLE 1

Formulation (Sterile Injection)

The components identified in the following tables were dissolved in distilled water for injection, and distilled water was added as needed to prepare the required concentration for injection. The solution was divided into 2 ml doses and placed into ampules, which were sealed, and sterilized by heating to prepare a sterile injection.

TABLE 1

| | Component | Amount |
|---|---|---|
| 10 mg preparation | fasudil hydrochloride (FAS) | 10 mg |
| | sodium chloride | 16 mg |
| | distilled water | ad lib. |
| | Total | 2 ml |
| 30 mg preparation | fasudil hydrochloride (FAS) | 30 mg |
| | sodium chloride | 16 mg |
| | distilled water | ad lib. |
| | Total | 2 ml |
| 60 mg preparation | fasudil hydrochloride (FAS) | 60 mg |
| | sodium chloride | 16 mg |
| | distilled water | ad lib. |
| | Total | 2 ml |
| compound of formula [I] hydrochloride | | |
| 10 mg preparation | ($R^1$ = hydroxy) | 10 mg |
| | sodium chloride | 16 mg |
| | distilled water | ad lib. |
| | Total | 2 ml |
| compound of formula [I] hydrochloride | | |
| 30 mg preparation | ($R^1$ = hydroxy) | 30 mg |
| | sodium chloride | 16 mg |
| | distilled water | ad lib. |
| | Total | 2 ml |
| compound of formula [I] hydrochloride | | |
| 60 mg preparation | ($R^1$ = hydroxy) | 60 mg |
| | sodium chloride | 16 mg |
| | distilled water | ad lib. |
| | Total | 2 ml |

EXAMPLE 2

Formulation (Tablets)

Tablets containing the compound in Table 2 were prepared by conventional methods.

TABLE 2

| | Component | Amount |
|---|---|---|
| 10 mg preparation | fasudil hydrochloride (FAS) | 10.0 mg |
| | crystalline cellulose | 25.0 mg |
| | lactose | 108.5 mg |
| | magnesium stearate | 1.5 mg |
| | carboxymethylcellulose calcium | 5.0 mg |
| | Total | 150.0 mg |
| 20 mg preparation | fasudil hydrochloride (FAS) | 20.0 mg |
| | crystalline cellulose | 25.0 mg |
| | lactose | 98.5 mg |

TABLE 2-continued

| Component | | Amount |
|---|---|---|
| | magnesium stearate | 1.5 mg |
| | carboxymethylcellulose calcium | 5.0 mg |
| | Total | 150.0 mg |
| | compound of formula [I] hydrochloride | |
| 10 mg preparation | ($R^1$ = hydroxy) | 10.0 mg |
| | crystalline cellulose | 25.0 mg |
| | lactose | 108.5 mg |
| | magnesium stearate | 1.5 mg |
| | carboxymethylcellulose calcium | 5.0 mg |
| | Total | 150.0 mg |
| | compound of formula [I] hydrochloride | |
| 20 mg preparation | ($R^1$ = hydroxy) | 20.0 mg |
| | crystalline cellulose | 25.0 mg |
| | lactose | 98.5 mg |
| | magnesium stearate | 1.5 mg |
| | carboxymethylcellulose calcium | 5.0 mg |
| | Total | 150.0 mg |

EXAMPLE 3

Inhibitory Activity of HIV Syncytia Formation a) Activity of the medicament on HIV-1 acute-phase infection:

METHOD

Cells obtained by culturing MOLT-4 (American Type Culture Collection ATCC CRL-1582) in RPMI medium (GIBCO Corp.) containing 10% FBS (fetal bovine serum: GIBCO Corp.) (culture condition: 37° C., 5% $CO_2$/95% air) were prepared to aliquot number of cells ($1\times10^5$ cells/50 µl). The cell suspension, 50 µl and the liquid preparation, 50 µl containing HIV-1 (LAV-1 strain, Wain-Hobson et al., Cell 40: 9–17, 1985) in RPMI medium with 10% FBS were put into each well of a 96 hole microplate and cultured for 48 hours (Infectious condition of MOLT-4 and HIV-1: M.O.I.= 4.0).

TEST GROUP CONTAINING THE COMPOUND

Each compound was dissolved in RPMI medium containing 10% FBS at the final concentration as shown in FIG. 1 to prepare the medicament solution. The medicament solution, 100 µl was added to the mixture of MOLT-4 cell preparation and HIV-1 preparation at the time of mixing with MOLT-4 and HIV-1 to prepare the final volume of the liquid, 200 µl. The number of formed syncytia were microscopically counted.

Tested compounds were: FAS (fasudil hydrochloride, Chem. Pharm. Bull., 40 (3), 770–773, (1992)), C kinase inhibitor H-7 (1-5-isoquinolinylsulfonyl)-2-methyl-piperazine, Sigma Corp.), and calmodulin kinase II inhibitor KN-62 (1-(N,O-bis-[5-isoquinolinylsulfonyl]-N-methyl-L-tyrosyl)-4-phenyl-piperazine, Sigma Corp., Neuroscience Lett., 129, 47 (1991)).

The control group without the compound was prepared by replacing the medicament solution, 100 µl.

Syncytium formation activity was calculated by comparing the syncytia formation in the test group to that of the control group in the following equation.

Syncytium formation activity=number of syncytia formed in the medicament-added group/number of syncytia formed in the no-medicament-added group.

RESULT

The results are shown in FIG. 1 in which the vertical axis shows syncytia formation activity and the horizontal axis shows the final concentration of the compound.

FAS (-o-) inhibits 90% of syncytia formation in concentrations of at least 1.0 µM. H-7 (-Δ-) and KN-62 (-□-) inhibit approximately 50% and 75%, respectively, in concentrations of 30 µM, and no inhibitory effects were observed in concentrations of 2.0 µM. The number of syncytia in the control group (no compound added) were 175±20. In conclusion, FAS inhibits cell infection by HIV virus particles. Accordingly, FAS is effective for suppression or prevention of HIV infection.

b) Activity of the medicament on HIV-1 chronic-phase infection:

METHOD

Cells obtained by culturing MOLT-4 (culture condition: 37° C., 5% $CO_2$/95% air, RPMI medium (GIBCO Corp.) containing 10% FBS) were adjusted to a preferable number of cells ($1\times10^5$ cells/50 µl). HIV-1 (LAV-1) preparation, 50 µl was added to the cell suspension, 50 µl and subjected to a mixing culture (infectious condition of HIV-1 to MOLT-4: M.O.I.=1). The infected cell mixture was cultured by exchanging a fresh culture medium every 3 days at a volume rate of 2:5. The culture was continued for more than 1 month to prepare persistent infected cells. The concentration of the persistent infected cells was adjusted to a preferable number of cells ($1\times10^5$ cells/50 µl ) (the persistent infected cell preparation).

Cell preparation without infection was prepared by culturing MOLT-4 (culture condition: 37° C., 5% $CO_2$/95% air, RPMI medium (GIBCO Corp.) containing 10% FBS) and adjusting the concentration to a preferable number of cells ($1\times10^5$ cells/50 µl).

The persistent infected cell preparation, 50 µl, was placed in the wells of a 96 hole microplate and the non-infected cell preparation, 50 µl, was added therein and cultured for 48 hours. Numbers of the formed syncytia were counted microscopically.

Figure 2:
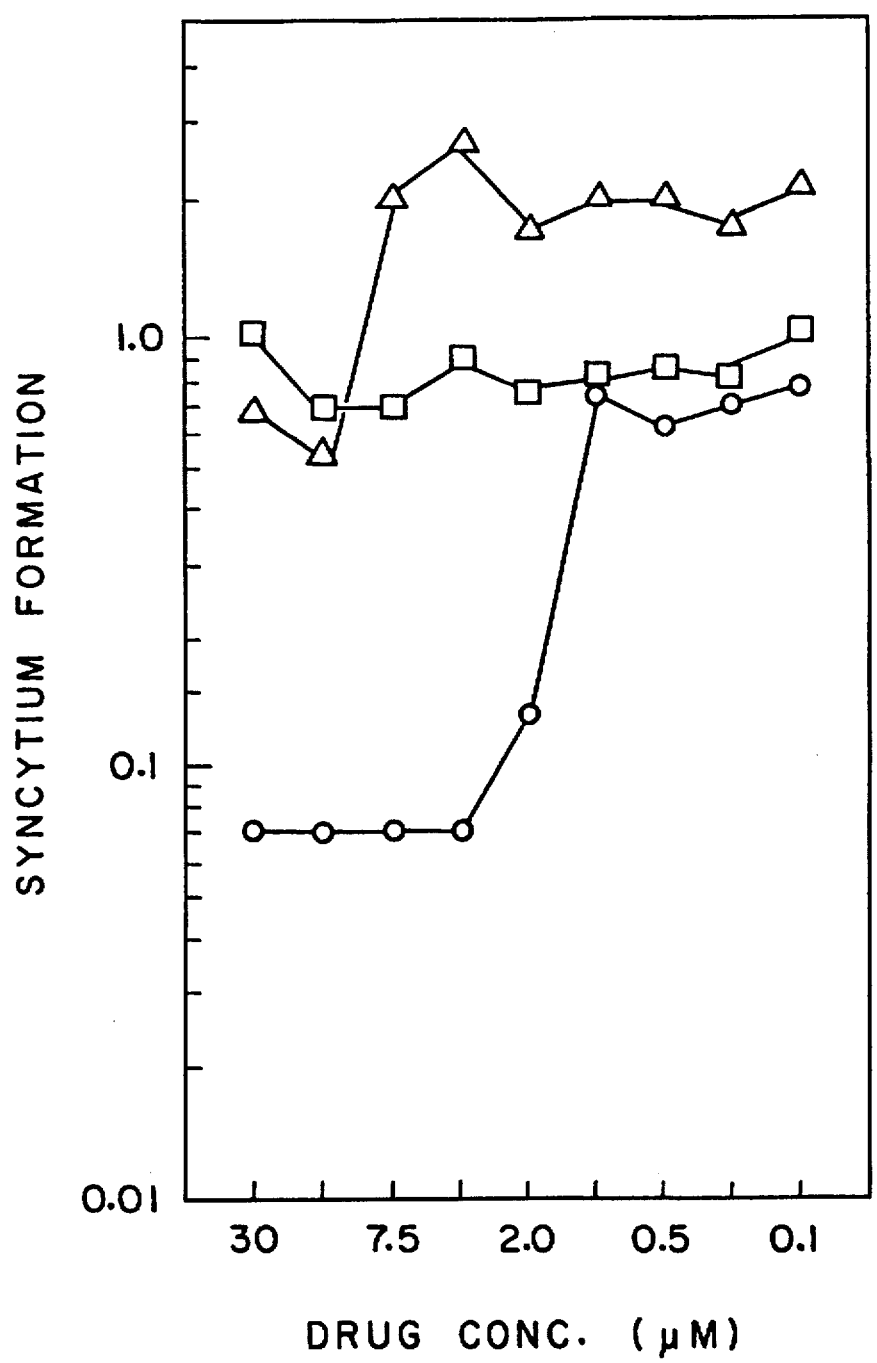
FIG. 2: action of the compound (result of assay on the inhibitory activity for syncytium formation) on chronic phase infection caused by HIV-1 in Example 3.

Each compound solution tested was added, 100 µl, at the time of mixing the persistent infected cell preparation with the non-infected cell preparation, to provide the final concentrations shown in FIG. 2 (medicament added test group).

The no-medicament-added group (control group) was prepared by replacing the compound solution, 100 µl.

RESULT

As shown in FIG. 2, FAS showed extremely high suppressive action on syncytium formation. FAS (-o-) showed inhibitory activity for syncytium formation in concentrations of at least 3.75 µM. H-7 (-Δ-) and KN-62 (-□-) showed no inhibitory activity for syncytium formation.

Viral transmission from persistent infected cells to non-infected cells was suppressed by FAS. Therefore, FAS indicated that it would suppress viral transmission in the blood and lymph node in patients infected with virus (especially HIV).

The medicament of the present invention showed effect at low drug concentrations in the suppression of viral infection and that of viral transmission (infection) between infected cells and non-infected cells. Accordingly, the medicament of the present invention is expected to be a medicament for prevention and treatment of viral infectious diseases such as HIV infectious diseases.

In the experiments shown in Examples 3, 4, 5 and 6, there were no cytotoxic findings for MOLT-4 cells by the medicament of the present invention.

EXAMPLE 4

Suppressive Action on Proliferation of HIV.

(Suppressive action on expression of Env (gp120) protein on the surface of cells.)

METHOD

Cells obtained by culturing MOLT-4 (culture condition: 37° C., 5% $CO_2$/95% air, RPMI medium (GIBCO Corp.) containing 10% FBS) were adjusted to a preferable number of cells ($1 \times 10^5$ cells/50 µl). The cell suspension, 50 µl, (infected with MOLT-4 and HIV-1: M.O.I.=1.0) was put in a 96 hole microplate and cultured for 1 hour to infect the cells.

A solution of the compound shown below, 100 µl, was added in each well and cultured for 5 days. The cultured solution was transferred into a plastic tube (Eppendorf Corp.) and centrifuged to collect the cells. The cells were treated with mouse anti-Env gp120 monoclonal antibody (Replingen Inc.) as a primary antibody and FITC (Fluorescein Isothiocyanate) labelled goat anti-mouse IgG (Cappel Corp.) as a secondary antibody to fluoresce. The number of fluorescent cells was fluoroscopically calculated by counting fluorescent cells according to an indirect fluorescent antibody technique (Techniques in HIV Research, Ed. A. Aldoriny and B. D. Walker, Stokton Press, New York, 1990).

Env positive cells (%) was calculated by the following equation:

Env positive cells (%)=(FITC) positive cells/total cells)× 100

Compounds: FAS, H-7 and KN-62.

Control: solution without compound was used.

RESULT

Figure 3:
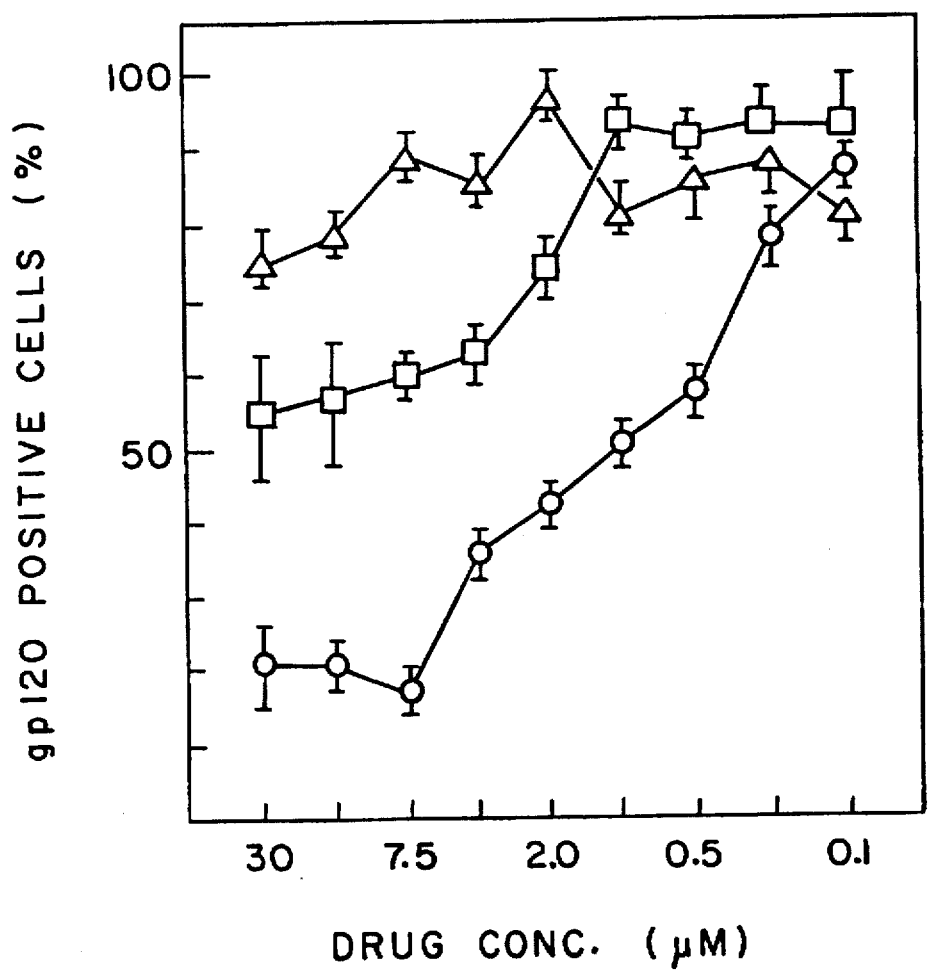
FIG. 3: suppressive action on proliferation of HIV-1 in Example 4.

The results are shown in FIG. 3. In FIG. 3, the vertical axis is the Env positive cells percentage (showing the mean plus and minus the standard deviation, n=3) and the horizontal axis is the concentration of the compound.

FAS (-o-) showed strong inhibitory activity for Env expression. KN-62 (-□-) showed weak inhibitory activity for Env expression, and H-7 (-Δ-) showed no significant inhibitory activity for Env expression.

Env protein is a structural protein of a retrovirus such as HIV-1 and exists on the surface of human T-cells and HIV-particles.

Expression of the Env protein indicates viral proliferation. These results indicate that FAS suppresses viral proliferation.

Accordingly, the medicament of the present invention was shown to be effective for prevention and treatment of viral infectious diseases such as retrovirus including HIV-1.

EXAMPLE 5

Suppressive action of HIV production (extracellular release from cells).

METHOD

Cells obtained by culturing MOLT-4 (culture condition: 37° C., 5% $CO_2$/95% air, RPMI medium (GIBCO Corp.) containing 10% FBS) were adjusted to a preferable number of cells ($1 \times 10^5$ cells/50 µl). The cell suspension, 50 µl, (infection with MOLT-4 and HIV-1: M.O.I.=1.0) were put in a 96 hole microplate and cultured for 1 hour to infect the cells.

A solution of the compounds shown below, 100 µl, was added in each well and cultured for 5 days. The cultured solution was transferred into a plastic tube (Eppendorf Corp.) and centrifuged. The amount of p24 gag protein in the cultured supernatant medium wa assayed by using an Abbott kit (ELISA: Dinabot Co.). FAS, H-7 and KN-62 were used as the compound, and a solution without the compound was used as a control.

RESULT

Figure 4:
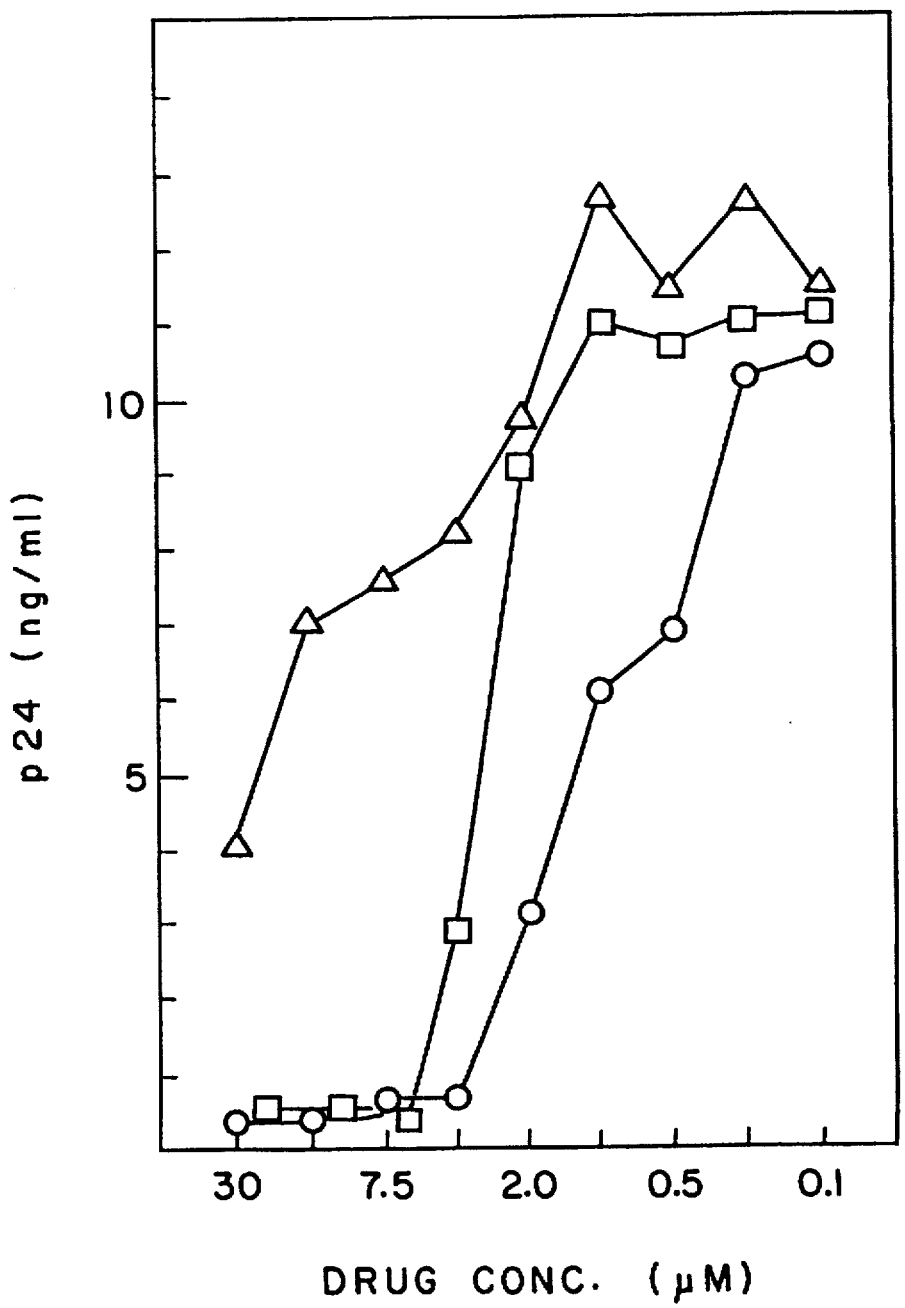
FIG. 4: suppressive action on generation of HIV-1 in Example 4.

The results are shown in FIG. 4. In FIG. 4, the vertical axis is the concentration of p24 gag protein antigen (ng/ml) and the horizontal axis is the concentration of the compound.

The addition of the FAS (-o-) decreased p24 gag protein in the cultured supernatant medium and suppressed HIV-1 generation. The activity of FAS to decrease the p24 gag protein is apparently stronger than that of H-7 (-Δ-) and KN-62 (-□-).

The p24 gag protein is an important protein for formation of a viral core in the construction of HIV-1 viral particles. The amount of p24 gag protein is proportional to the amount of infectious virus. Accordingly, FAS suppresses HIV-1 formation. The medicament of the present invention has been shown to be effective for prevention and treatment of viral infectious diseases including HIV-1 infectious disease.

EXAMPLE 6

Comparison of suppressive activity of HIV proliferation with FAS and other anti-HIV drugs.

METHOD

Experiments were conducted by the same method as in Example 3.

The medicaments used in this experiment were compounds of the present invention (FAS, and a compound of formula [I] where $R^1$ is hydroxy as in the above-mentioned Japanese Patent Unexamined Publication No. 61-152658), ddI (Sigma Corp.) and AZT (Sigma Corp.) which are used as medicaments for the treatment of AIDS, and dextran sulfate (Sigma Corp.).

RESULT

Figure 5:
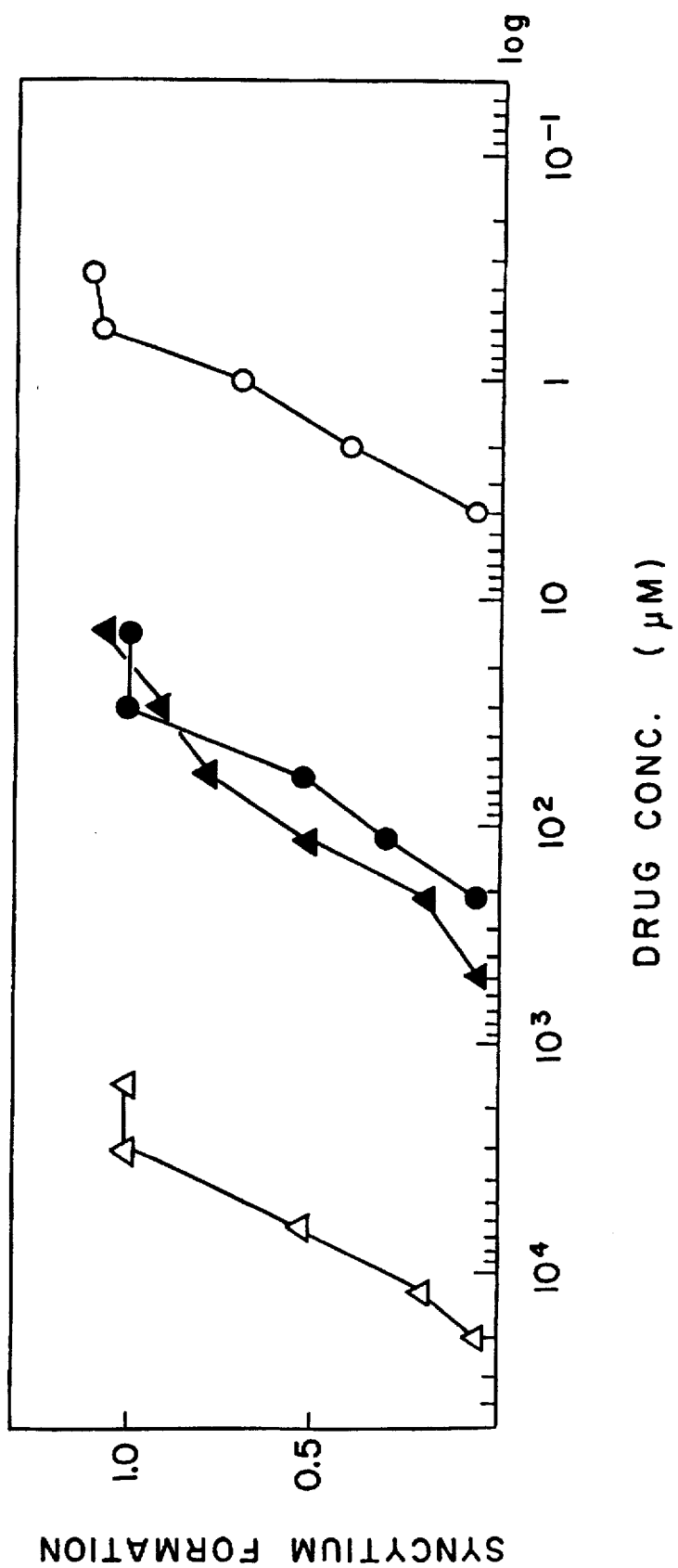
FIG. 5: comparison of suppressive action on proliferation of HIV-1 (inhibitory action on syncytium formation) with FAS and other compounds.

The results are shown in FIG. 5, in which the vertical axis is syncytia formation activity and the horizontal axis is the concentration of the compound.

The 50% inhibitory concentration of dextran sulfate (-Δ-), ddI (-▲-), AZT (-●-) and FAS (-o-) are approximately 60 mM, 100 µM, 50 µM and 800 nM, respectively. As is apparent, with regard to the inhibitory activity of syncytium formation of HIV-1, FAS showed higher sensitivity than dextran sulfate, ddI and AZT. The present compound where $R^1$ is hydroxy inhibited the formation of syncytium of HIV-1.

Syncytium formation of HIV-1 is a marker of HIV-1 infection, and infection and proliferation of HIV-1 are markers of the onset of AIDS, a retroviral infectious disease.

The medicament for prevention and suppression of the present invention is hopeful as a more effective anti-HIV drug than the known anti-HIV drugs.

EXAMPLE 7

The compound of the present invention was confirmed to have no hematologic toxicity.

METHOD a) Blood coagulation time:

Rabbits (male, Japanese white, body weight 2-3 kg, Oriental Yeast Co.) were used. Blood was collected from an ear vein, a 1/10 volume of 3.8% sodium citrate was added thereto, and the mixture was centrifuged at 3,000 rpm for 20 minutes. After adding the test compound to the resultant plasma, activated partial thromboplastin time (APTT) and prothrombin time (PT) were measured by using a coagulometer (Coagtec, Coagtec TE600, EMRA; KC-10A, Baxter).

The compounds used were compounds of the present invention (FAS, and the compound of formula [I] where $R^1$ is hydroxy (Japanese Patent Unexamined Publication No. 61-152658), and heparin (Shimizu Seiyaku K.K.).

b) Platelet aggregation:

Rabbits (male, Japanese white, body weight 2–3 kg, Oriental Yeast Co.) were used. Blood was collected from an ear vein, a 1/10 volume of 3.8% sodium citrate was added thereto, and the mixture was centrifuged at 1,000 rpm for 10 minutes.

The supernatant separated by this action was designated platelet rich plasma (PRP), and the precipitate was further centrifuged at 3,000 rpm for 10 minutes to obtain a further supernatant, which was designated platelet poor plasma (PPP).

The number of platelets in the PRP was adjusted to $3\times10^5$ plate/µl by adding the PPP. A test sample was added to the PRP. After 1 minute, a prepared aqueous solution of ADP (adenosine diphosphate, Sigma Corp.) was added at the final concentration of 5 µM, or an aqueous solution of collagen (Sigma Corp.) was added at the final concentration of 5 µg/ml. The agglutination reaction was measured by using an agglico meter (NBS HEMA TRACER VI). The inhibition rate was calculated by comparing the maximum optical transmittance in samples with the compound to the maximum optical transmittance in samples with a physiological saline.

The compounds used were compounds of the present invention (FAS, and the compound of formula [I] where $R^1$ is hydroxy (Japanese Patent Unexamined Publication No. 61-152658) and adenosine (Sigma Corp.).

RESULT a) Blood coagulation time:

As shown in Table 3, no effects of the compounds of the present invention on APTT and PT on rabbit plasma were observed. Heparin clearly extended APTT and PT. FAS and the compound of formula [I] were $R^1$ is hydroxy have no effect on blood coagulation time.

TABLE 3

| | Action on blood coagulation time | | |
|---|---|---|---|
| | N | APTT(s) | PT(s) |
| Control FAS ($R^1$ = H) | 4 | 16.9 ± 0.8 | 7.3 ± 0.4 |
| 10 µM | 4 | 16.4 ± 0.8 | 7.1 ± 0.6 |
| 30 µM | 4 | 16.0 ± 0.8 | 7.1 ± 0.5 |
| 100 µM | 4 | 16.3 ± 0.8 | 7.6 ± 0.9 |
| Heparin | | | |
| 0.05 U/ml | 4 | 19.9 ± 1.4 | 7.2 ± 0.6 |
| 0.5 U/ml | 4 | 91.8 ± 11.4** | 9.3 ± 1.2 |
| 5 U/ml | 4 | N.T. | 18.5 ± 0.6** |
| Control | 4 | 21.2 ± 0.5 | 5.8 ± 0.1 |
| Compound of the formula [I] | | | |
| ($R^1$ = OH) | | | |
| 30 µM | 4 | 20.2 ± 0.4 | 5.6 ± 0.1 |
| 100 µM | 4 | 20.1 ± 0.4 | 5.5 ± 0.1 |

TABLE 3-continued

| | Action on blood coagulation time | | |
|---|---|---|---|
| | N | APTT(s) | PT(s) |
| Heparin | | | |
| 0.05 U/ml | 4 | 22.3 ± 0.3 | 5.6 ± 0.1 |
| 0.5 U/ml | 4 | 77.1 ± 1.9** | 7.6 ± 0.1** |

**: $p < 0.01$ compared with control (Dunnett's test)
N.T.: not test
mean ± S.E.

b) Platelet aggregation:

As shown in Table 4, no effects of the compounds of the present invention on ADP coagulation and collagen coagulation on rabbit platelets were observed. Adenosine suppressed ADP coagulation and collagen coagulation.

TABLE 4

| | Action on platelet aggregation | | |
|---|---|---|---|
| | | Platelet aggregation rate (%) | |
| | N | ADP | Collagen |
| Control FAS ($R^1$ = H) | 5 | 64.5 ± 7.4 | 78.7 ± 6.3 |
| 10 µM | 5 | 66.1 ± 8.7 | 79.9 ± 5.6 |
| 30 µM | 5 | 69.5 ± 10.5 | 83.8 ± 4.3 |
| 100 µM | 5 | 59.3 ± 8.0 | 58.7 ± 7.4 |
| Adenosine | | | |
| 10 µM | 5 | 35.5 ± 3.8* | 46.4 ± 6.0** |
| Control | 4 | 66.3 ± 1.4 | 82.3 ± 1.6 |
| Compound of the formula [I] | | | |
| ($R^1$ = OH) | | | |
| 10 µM | 4 | 63.0 ± 2.3 | 80.0 ± 1.7 |
| 30 µM | 4 | 63.8 ± 2.9 | 79.3 ± 1.1 |
| 100 µM | 4 | 64.3 ± 3.8 | 81.0 ± 1.2 |

*: $P < 0.05$,
**: $P < 0.01$ Comparison with control (Dunnett's test)
mean ± S.E.

In vitro concentration of the compounds of the present invention, approximately 30 µM, used in Examples 3, 4, 5, and 6 showed no adverse effects on blood coagulation and platelet aggregation.

As a result, the medicament of the present invention is very safe.

EXAMPLE 8

Acute toxicity of the compounds of the present invention were conducted on rats and mice, and low toxicity was confirmed. The results are shown in Table 5.

TABLE 5

| Compound (formula [I]) | Animals (strain, age in weeks) | Administration route | Sex | Result $LD_{50}$ (mg/kg) |
|---|---|---|---|---|
| $R^1$ = H | rats (Jcl: Wistar, 5 weeks) | i. v. | male | 59.9 |
| | | | female | 63.9 |
| | | p. o. | male | 335.0 |
| | | | female | 348.0 |

TABLE 5-continued

| Compound (formula [I]) | Animals (strain, age in weeks) | Administration route | Sex | Result $LD_{50}$ (mg/kg) |
|---|---|---|---|---|
| | | s. c. | male | 123.2 |
| | | | female | 128.3 |
| $R^1 = H$ | mice (Slc: ddy, 5 weeks) | i. v. | male | 63.7 |
| $R^1 = OH$ | | i. v. | male | 119.3 |

Example 9

Inhibitory action for plaque formation of Herpes simplex virus type I and parainfluenza virus.

METHOD

Experiments were performed according to a method described in Antiviral Chemistry and Chemotherapy, 5 (6), 366–371, 1994 and Experimental Virology, Ed. by NIH Japan alumni assoc., Maruzen Publ. 1982, p. 65–78 or p. 331–340.

Vero cells cultured in the medium (Dulbecco's modified MEM added with 10% FBS) were detached by trypsin (Sigma Corp.). The detached cells were suspended by $2\times10^5$ cells/ml in the same medium, and placed in the wells of a 48 hole plate. The plate was incubated at 37° C. under 5% $CO_2$ for about one day to complete a full-sheet of the cells in all wells. After incubation, cultured supernatant was removed. A solution (50 µl) containing the compound diluted with 4-fold stepwise dilution by virus culture medium (MM: Dulbecco's modified MEM added with 2% FBS), was added thereto.

A viral solution, 50 µl, in which the number of virus (parainfluenza virus or Herpes simplex virus type I) was adjusted to about 50 pfu (plaque forming unit)/50 µl by MM, was added to each well. MM 400 µl containing 1% methylcellulose was added in each well to provide a compound-added test group. A control group was prepared by adding the viral culture medium without adding the test compound.

The groups were incubated at 37° C. under 5% $CO_2$ for three days to form plaques and the number of plaques in each well was counted.

The test compounds were FAS, and the compound of formula [I] where $R^1$ is hydroxy. The final concentration of the compound in the solution was set to 100, 25, 6.3 and 1.6 µg/ml, respectively. Each test group included 2 wells and a mean of the plaque numbers was obtained.

The resultant effect on herpes simplex virus type I is shown in Table 6, and the effect on parainfluenza virus is shown in Table 7.

TABLE 6

Effect on Herpes simplex virus type I

| | Plaque No. | |
|---|---|---|
| Concentration (µg/ml) | FAS ($R^1 = H$) | Compound of the formula [I] ($R^1 = OH$) |
| 100 | 0 | 37.5 |
| 25 | 49 | 56 |
| 6.3 | 46 | 51 |
| 1.6 | 51 | 51 | value indicated is a mean of two lines
No. of plaques in control group is 51

As shown in Table 6, the compounds of the present invention inhibited the formation of plaques, depending on the dose.

TABLE 7

Effect on Parainfluenza virus

| | Plaque No. | |
|---|---|---|
| Concentration (µg/ml) | FAS ($R^1 = H$) | Compound of the formula [I] ($R^1 = OH$) |
| 100 | 3.5 | 4.5 |
| 25 | 36 | 59 |
| 6.3 | 50.5 | N. T. |
| 1.6 | N. T. | N. T. | value indicated is a mean of two lines
No. of plaques in control group is 51.5
N. T. = not tested The effect on parainfluenza virus is shown in Table 7, in which the compound of the present invention inhibited the formation of plaques by parainfluenza virus in RNA virus. Formation of plaques is a marker of viral infection and viral proliferation. The compound of the present invention inhibited proliferation and infection for Herpes simplex virus in DNA virus and parainfluenza virus in RNA virus.

In conclusion, the compounds of the present invention, such as FAS, showed suppressive or preventive effects on DNA viral infection and RNA viral infection.

As clearly shown in the above experimental results, the medicament of the present invention is a useful medicament for prevention and treatment of viral infectious diseases.

What is claimed is:

1. A method for treatment of viral infectious diseases comprising the step of administering to a patient in need of said treatment a medicament containing an effective amount of a compound of the formula

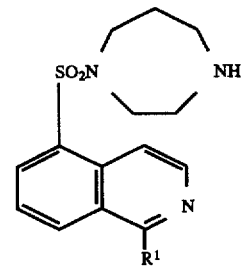

wherein $R^1$ is hydrogen or hydroxy, or an acid addition salt thereof as an active ingredient.

2. The method according to claim 1, wherein the viral infectious diseases are retroviral infectious diseases.

3. The method according to claim 2, wherein the retroviral infectious diseases are HIV infectious diseases or adult T-cell leukemia.

4. The method according to claim 1, further comprising the step of preparing said medicament for injection.

5. The method according to claim 4, wherein said medicament contains 0.001–20 weight percent of said active ingredient.

6. The method according to claim 5, wherein said medicament contains 0.01–10 weight percent of said active ingredient.

7. The method according to claim 4, further comprising the step of administering the active ingredient at a rate of 0.01–25 mg/kg/day.

8. The method according to claim 7, wherein the active ingredient is administered at a rate of more than 1 mg/kg/day.

9. The method according to claim 1, further comprising the step of preparing said medicament for peroral administration.

10. The method according to claim 8, wherein said medicament contains 0.01–100 weight percent of said active ingredient.

11. The method according to claim 9, further comprising the step of administering the active ingredient at a rate of 0.02–40 mg/kg/day.

12. The method according to claim 11, wherein the active ingredient is administered at a rate of more than 0.5 mg/kg/day.

13. The method according to claim 12, wherein the active ingredient is administered at a rate of more than 1 mg/kg/day.

14. The method according to claim 13, wherein the active ingredient is administered at a rate of more than 4 mg/kg/day.

15. A method for suppressing viral infection, transmission, and growth, comprising the step of administering to a patient in need of such treatment a medicament containing an effective amount of a compound of the formula

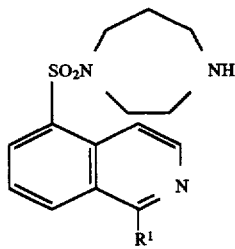

wherein $R^1$ is hydrogen or hydroxy, or an acid addition salt thereof as an active ingredient.

16. The suppressive method according to claim 15, wherein the virus is retrovirus.

17. The suppressive method according to claim 16, wherein the retrovirus is HIV.

18. The suppressive method according to claim 15, further comprising the step of preparing said medicament for injection.

19. The suppressive method according to claim 18, wherein said medicament contains 0.001–20 weight percent of said active ingredient.

20. The suppressive method according to claim 19, wherein said medicament contains 0.01–10 weight percent of said active ingredient.

21. The suppressive method according to claim 18, further comprising the step of administering the active ingredient at a rate of 0.01–25 mg/kg/day.

22. The suppressive method according to claim 21, wherein the active ingredient is administered at a rate of more than 1 mg/kg/day.

23. The suppressure method according to claim 15, further comprising the step of preparing said medicament for peroral administration.

24. The suppressive method according to claim 23, wherein said medicament contains 0.01–100 weight percent of said active ingredient.

25. The suppressive method according to claim 23, further comprising the step of administering the active ingredient at a rate of 0.02–40 mg/kg/day.

26. The suppressive method according to claim 25, wherein the active ingredient is administered at a rate of more than 0.5 mg/kg/day.

27. The suppressive method according to claim 26, wherein the active ingredient is administered at a rate of more than 1 mg/kg/day.

28. The suppressive method according to claim 27, wherein the active ingredient is administered at a rate of more than 4 mg/kg/day.

29. A method for suppressing Env expression, comprising the step of administering to a patient in need of such treatment a medicament containing an effective amount of a compound of the formula

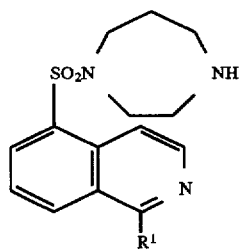

wherein $R^1$ is hydrogen or hydroxy, or an acid addition salt thereof as an active ingredient.

30. A method for suppressing viral generation, comprising the step of administering to a patient in need of such treatment a medicament containing an effective amount of a compound of the formula

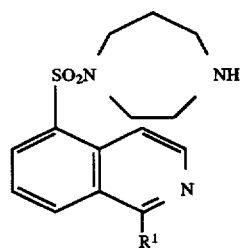

wherein $R^1$ is hydrogen or hydroxy, or an acid addition salt thereof as an active ingredient.

31. A method for suppressing viral syncytium formation, comprising the step of administering to a patient in need of such treatment a medicament containing an effective amount of a compound of the formula

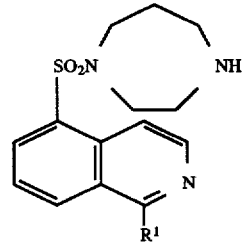

wherein $R^1$ is hydrogen or hydroxy, or an acid addition salt thereof as an active ingredient.

* * * * *